US00PP31932P2

(12) United States Plant Patent
Bédard

(10) Patent No.: US PP31,932 P2
(45) Date of Patent: Jul. 7, 2020

(54) ROSE PLANT NAMED 'WEKPUMPAHOR'

(50) Latin Name: *Rosa hybrida*
Varietal Denomination: WEKpumpahor

(71) Applicant: Gardens Alive! Inc., Greendale, IN (US)

(72) Inventor: Christian Bédard, Rancho Cucamonga, CA (US)

(73) Assignee: Gardens Alive! Inc., Greendale, IN (US)

( * ) Notice: Subject to any disclaimer, the term of this patent is extended or adjusted under 35 U.S.C. 154(b) by 0 days.

(21) Appl. No.: 16/501,780

(22) Filed: Jun. 3, 2019

(51) Int. Cl.
*A01H 5/02* (2018.01)
*A01H 6/74* (2018.01)

(52) U.S. Cl.
USPC ..... Plt./107
CPC ..... *A01H 6/749* (2018.05)

(58) Field of Classification Search
USPC ..... Plt./107
CPC ..... A01H 6/749; A01H 5/02
See application file for complete search history.

*Primary Examiner* — Keith O. Robinson
(74) *Attorney, Agent, or Firm* — Barbara Campbell; Cochran Freund & Young LLC

(57) ABSTRACT

A new and distinct variety of shrub rose having a compact bushy plant growth habit, suitable for outdoor garden decoration, flowers continuously during the growing season, has excellent resistance to common fungal diseases that are present in Ohio, and has pink flowers, is disclosed.

1 Drawing Sheet

Genus and species: *Rosa hybrida.*
Denomination: 'WEKpumpahor'.

BACKGROUND

'WEKpumpahor' is a new and distinct variety of shrub rose. 'WEKpumpahor' originated from a controlled hybridization in April to June 2007 in Pomona, Calif. between the female parent 'WEKmongros' (U.S. Plant Pat. No. 21,605) and the male parent 'WEKcisbako' (U.S. Plant Pat. No. 18,552).

The resulting seeds from the hybridization were planted and evaluated. 'WEKpumpahor' was selected between July to August 2008 in Pomona, Calif. 'WEKpumpahor' was first asexually propagated in August 2008 in Wasco, Calif. on its own root cuttings, and subsequently by budding and grafting on the plant/rootstock of *Rosa hybrida* 'Dr. Huey' (unpatented).

Other subsequent asexual propagations were conducted in controlled environments in Pomona, Calif. and Tipp City, Ohio and demonstrate that 'WEKpumpahor' reproduces true to type in successive generations of asexual reproduction via softwood cuttings, budding, and grafting.

SUMMARY

The following are the most outstanding and distinguishing characteristics of this new variety when grown under normal horticultural practices in Pomona, Calif. and Tipp City, Ohio.

1. A shrub rose having a compact bushy plant growth habit, suitable for outdoor garden decoration;
2. Flowers continuously during the growing season;
3. Has excellent resistance to common fungal diseases that are present in Ohio; and
4. Has pink flowers.

DESCRIPTION OF THE PHOTOGRAPH

This rose plant is illustrated by the accompanying photograph which shows the individual parts of the plant. The colors shown are as true as can be reasonably obtained by conventional photographic procedures. The photograph is of the parts of a 3 to 4-year old rose plant grown outdoors in Tipp City, Ohio in August 2018. The colors shown are as true as can be reasonably obtained by conventional photographic procedures.

The photograph shows from top to bottom, starting at the top (first) row from left to right, three individual flowers in full bloom, from the newly full bloom to older full bloom; the second row shows from left to right a flowering stem with multiple buds and a flower beginning to bloom, and a shorter flowering stem with multiple buds and foliage; the third row shows from left to right, an immature flowering stem with foliage and buds, the lower surface of an individual petal (top) and the upper surface of an individual petal (bottom), and the reproductive parts of the flower with the petals removed; the fourth row shows from left to right, the upper surface of the compound leaf, and the lower surface of the compound leaf; and the fifth (bottom) row shows an individual stem with only thorns of the plant.

DETAILED DESCRIPTION

The following detailed descriptions set for the distinctive characteristics of 'WEKpumpahor'. The data which define these characteristics were collected outdoors in Tipp City, Ohio in August 2018 from 3 to 4-year old plants. The phenotype of this new variety will vary somewhat with variation in environmental, climatic, and cultural conditions as it has not been tested in other environments. Color references are to The R.H.S. Colour Chart of The Royal Horticultural Society of London (R.H.S.) 2001.

Classification:

*Family.*—Rosaceae.
*Species.*—*Rosa hybrida.*
*Common name.*—Shrub rose.
*Variety.*—'WEKpumpahor'.

Parentage:

*Female parent*.—'WEKmongros' (U.S. Plant Pat. No. 21,605).

*Male parent*.—'WEKcisbako' (U.S. Plant Pat. No. 18,552).

Growth: The plant has a dwarf-like bushy compact growth habit, about 100 cm to about 120 cm in height and about 75 cm to about 90 cm spread at the widest point, with full branching. It displays vigorous growth and the canes are of light to medium caliper for the class, about 0.5 cm to about 1.0 cm in diameter at the widest point.

Stems: The color of the major stems is near RHS 147B. The major stems are rough in texture and they bear several prickles that are about 5 mm to about 7 mm in length. The large prickles, which are about 5.0 mm or greater in length, are hooked moderately downward with a medium length base, which is approximately 5.0 mm in length; prickle color is near RHS 147C when young and near RHS 200D when on old wood. The major stem bears several small prickles of similar shape and coloration. There are no fine coarse hairs. The color of the branches is near RHS 147B. The branches are rough in texture and they bear several large prickles which are of similar size, shape and color to the large prickles on the major stems. The branches bear several small prickles of similar shape and coloration as on the main stems. There are no fine or coarse hairs. The color of the new shoots is near RHS 147B often suffused with near RHS 187B. The new shoots are rough in texture and they bear several prickles which are of similar size and shape to the large prickles on the major stems; prickle color is near RHS 147B. There are no fine hairs present.

Foliage: The compound leaves are usually comprised of three to seven leaflets and are borne in normal quantities of about 200 to 250 compound leaves. The five-leaflet leaves are about 9 cm to about 10 cm in length and about 7.5 cm to about 8.0 cm in width at the widest point, leathery in texture on both sides, and matte in finish on the upper side and matte in finish on the underside. The leaves have a pinnate venation pattern. The terminal leaflets are about 4.3 cm to about 4.6 cm in length and about 2.8 cm to about 3.1 cm in width at the widest point, shaped oval to ovate with acuminate apices and rounded bases. Their margins are doubly serrate. The upper surface color of the mature leaf is near RHS 139A. The lower surface color of the mature leaf is near 147B. The lower and upper surface colors of the leaf veins on the mature leaf are similar in coloration to the upper and lower surfaces colors of the mature leaf. The upper surface of an immature leaf is between RHS 187A and RHS 187B. The lower surface color of the young leaf is near RHS 187B. The lower and upper colors of the leaf veins on the young leaf are similar in coloration to the upper and lower surfaces colors of the young leaf. The rachis is about 5 cm to about 5.5 cm in length, about 1.0 mm in width at the widest point, and somewhat rough. The upper surface is moderately grooved with few stipitate glands on the edges of the grooves. The lower surface of the rachis is somewhat rough with stipitate glands and small prickles. The rachis color is near RHS 139A on the upper surface and near RHS 146B on the lower surface, often moderately suffused on the young leaves with near RHS 187B. The stipules are about 1.0 cm to about 1.4 cm in length and of medium width, about 5 mm to about 6 mm, with medium straight points that usually turn out at an angle of more than 45 degrees toward the stem. The lower and upper surface color of the stipule is near RHS 146C. The upper and lower surfaces of the stipules are smooth in texture. The petiole is average in caliper and somewhat rough. The upper surface is shallowly grooved with some stipitate glands on the edges of the grooves. The lower surface of the rachis is somewhat rough with some stipitate glands. The petiole is about 3 mm to about 4 mm in length and about 1.0 mm to about 1.3 mm in width at the widest point. The petiole color is near RHS 146B on the lower surface and near RHS 187B on the upper surface, heavily suffused on the young leaves with near RHS 187B.

Flower: 'WEKpumpahor' usually bears its flowers in clusters of three to five per stem. Flowers are borne in flat to slightly rounded clusters on strong short stems, where the stems are about 10 cm to 15 cm in length. The cluster ranges from about 8 cm to about 12 cm in diameter. Outdoors, the plant blooms abundantly and nearly continuously during the growing season. The flowers have a slight apple-like fragrance. The shape of the flower is slightly cupped. The receptacle of the flower is medium in length, about 7 mm to about 9 mm, and average in caliper, about 5 mm to about 6 mm in diameter. The receptacle is funnel shaped in form. Its surface is smooth with very moderately thick dry fleshy walls. The receptacle color is near RHS 146B.

Flower bud: Before the calyx breaks, the bud is about 1.2 cm to about 1.5 cm in diameter at the widest point, about 2 cm to about 2.3 cm in length, and pointed to ovoid in shape with a conspicuous neck. The surface of the bud bears 3 to 5 lightly foliaceous appendages that extend slightly above the bud. Bud color before the calyx breaks is near between RHS 137C and RHS 137D. As the petals open (after the calyx breaks), the bud is about 1.7 cm to about 1.9 cm in diameter at the widest point, about 2.8 cm to about 3.0 cm in length, and pointed to ovoid in form.

Petals and petaloids: The substance of the petals is somewhat leathery, of medium thickness, with upper surfaces satiny and under surfaces matte. The petals are about 3.3 cm to about 3.5 cm in length and about 3.4 cm to about 3.6 cm in width at the widest point. Petal margins are entire. The outer petals are ovate to obovate to orbicular in shape with apices somewhat rounded to slightly obcordate. The inner petals are oval to ovate to obovate in shape with apices rounded to slightly obcordate. Petaloids are about 1.0 cm to about 2.3 cm in length and about 0.4 cm to about 1.4 cm in width at the widest point. Petaloids are spatulate to oblong in shape with somewhat rounded apices. The color of the lower and upper surfaces of the newly opened petals is between RHS 67C and RHS 67D. At the point where the petal attaches, there is a small zone of near 3C. The color of the upper surfaces of the newly opened petals is between RHS 67C and RHS 67D. At the point where the petal attaches, there is small zone of near RHS 3C.

Sepals: The sepals are 5 or 6 per flower, about 1.3 cm to about 1.5 cm. in length and about 0.7 cm to about 0.8 cm. in width at the widest point. The lower surface color of the sepal is near between RHS 137C and RHS 137D sometimes lightly suffused, especially on the side exposed to the sun, with near between RHS 183C and RHS 183D. The lower surface of the sepal is moderately rough and bears between 0 to 5 foliaceous appendages with some stipitate glands. The upper surface color of the sepal is near RHS 138B. The upper surface of the sepal is edged with fine wooly tomentum; sepal margins are entire and lined with many numerous stipitate glands and hairs. The sepals are permanent, and spear-shaped to recurved in shape with acute apices. The receptacle of the flower is somewhat short in length, about 5 mm to about 6 mm and average in caliper, about 5 mm to about 6 mm in diameter. The receptacle is somewhat ovoid to oblong in form. Its surface is very smooth with somewhat thin fleshy walls. The receptacle color is near between RHS 137B and RHS 137C.

Peduncle: The peduncle is about 3 cm to about 4 cm in length, of slender caliper, about 2 mm to about 3 mm in diameter, and erect. It is almost entirely rough, with 30 to 35 stipitate glands and 11 to 15 small prickles less than 4.0 mm in length and with a base of 3.0 mm. Peduncle color is near RHS 146C.

Newly open flower: The lower and upper surface color of the outer petals is near between RHS 67C and RHS 67D. At the point where the petal attaches, there is a small zone of near RHS 3C, which is the basal spot of the petal, and is about 3 mm in length and 3 mm in width and extending out from the basal spot, is a zone of about RHS 2D that is about 3 mm wide. The upper surface color of the outer petals is near RHS 67C fading to RHS 67D nearer to point of attachment. The lower and upper surface color of the intermediate petals is RHS 67C to RHS 67D nearer the point of attachment. The upper surface color of the intermediate petals is near between RHS 67C and RHS 67D. The lower and upper surface color of the inner petals is near between RHS 67C and RHS 67D. The upper surface color of the inner petals is near RHS 67C and RHS 67D. The under and upper surface colors of the petaloids are similar in coloration to the upper and under surfaces of the intermediate and inner petals. The general tonality of the newly opened flower is between RHS 67C and RHS 67D.

Three-day-old flower: The lower and upper surface color of the outer petals is near RHS N66D. At the point where the petal attaches, there is a large zone of near RHS 158D. The upper surface color of the outer petals is near RHS N66D. At the point where the petal attaches, there is a large zone near RHS 158D. The lower and upper surface color of the inner petals is near RHS N66D. The upper surface color of the inner petals is near RHS N66D. The lower and upper surface colors of the petaloids are similar in coloration to the upper and under surfaces of the intermediate and inner petals. The general tonality of the three-day-old flower is near RHS N66D. On the spent bloom, the petals drop off cleanly and are not particularly affected by cold, hot, wet, or dry weather. In August in Tipp City, Ohio blooms on the bush growing outdoors generally last about four to five days. Cut roses from plants grown outdoors and kept at normal indoor living temperatures generally last about five days.

Fully-open flower: When fully open, the bloom ranges from about 10 cm to about 11 cm in diameter. Petalage is semi-double with about 15 to 20 petals and about 1 to 3 petaloids irregularly arranged. When partially open, the bloom form is high-centered, and the petals are somewhat spiraled with petal edges reflexed outward. When fully open, the bloom form is flat, and the petals are moderately flat to imbricated with petal edges somewhat reflexed. Hips and seed formation: Hips have been observed on this variety when grown in Tipp City, Ohio. They are average in length is about 1.6 cm to about 1.8 cm, ovoid to oblong in form, and near RHS N30A in color when ripe. The hip surface is smooth with thick fleshy walls. The seeds are smooth in texture, approximately 1 to 7 per hip, about 4 mm to about 5 mm in diameter at the widest point and near RHS 164D in color.

Male reproductive organs: Stamens are average in number, average about 85, and are arranged regularly about the pistils. The filaments are of medium length, about 0.6 cm to about 1.0 cm, few without anthers. Filaments are near RHS 13C in color. The anthers are medium to large for the class and all open at approximately the same time. Anther color when immature is near RHS 15C on the external part and near RHS 15D on the internal part. Anther color at maturity is near RHS 165C on the external part and near RHS 165A on the internal part. Pollen is abundant and near RHS 163B in color.

Female reproductive organs: Pistils vary in number, average about 35. The styles are somewhat uneven, short in length, about 3 mm to about 4 mm, average in caliper which is 1.0 mm and bunched. Stigma color is near RHS 158A. Style color is near RHS 53D. Ovaries are enclosed in the calyx. The ovaries are of average size, 1.0 mm length by 1.0 mm in width, and near RHS 158C color.

Disease resistance: The plant displays an average above average degree of resistance to powdery mildew (*Sphaerotheca pannosa*), downy mildew (*Peronospora sparsa*), black spot (*Diplocarpon rosae*) and rust (*Phragmidium* sp.) as compared to other commercial varieties grown under comparable conditions in Tipp City, Ohio under no spray conditions. The plant's winter hardiness has been tested down to −17 F and found to be hardy without any winter protection.

COMPARISON WITH PARENTAL AND COMMERCIAL LINES

'WEKpumpahor' may be distinguished from the female parent, 'WEKmongos' (U.S. Plant Pat. No. 21,605) by the following combination of characteristics: 'WEKpumpahor' has pink flowers, and the female parent has caramel orange flower color. 'WEKpumpahor' averages 15 to 20 petals per flower, while the female parent averages 25 to 30 petals per flower.

'WEKpumpahor' may be distinguished from the male parent, 'WEKcisbako' (U.S. Plant Pat. No. 18,552) by the following combination of characteristics: 'WEKpumpahor' has pink flowers, while the male parent has bright red flowers. 'WEKpumpahor' has 15 to 20 petals per flower, while the male parent has 5 to 7 petals per flower.

'WEKpumpahor' may be distinguished from its closest commercially available cultivar, 'RADcon' (U.S. Plant Pat. No. 15,070) by the following combination of characteristics: 'WEKpumpahor' has 15 to 20 petals per flower, while 'RADcon' has 5 to 7 petals per flower. 'WEKpumpahor' has larger longer foliage, 9 cm to 10 cm long and larger flowers, 10 cm to 11 cm, while 'RADcon' has smaller foliage, 7 cm long, and smaller flowers, 7 cm.

I claim:

1. A new and distinct variety of rose plant designated 'WEKpumpahor' as illustrated and described herein.

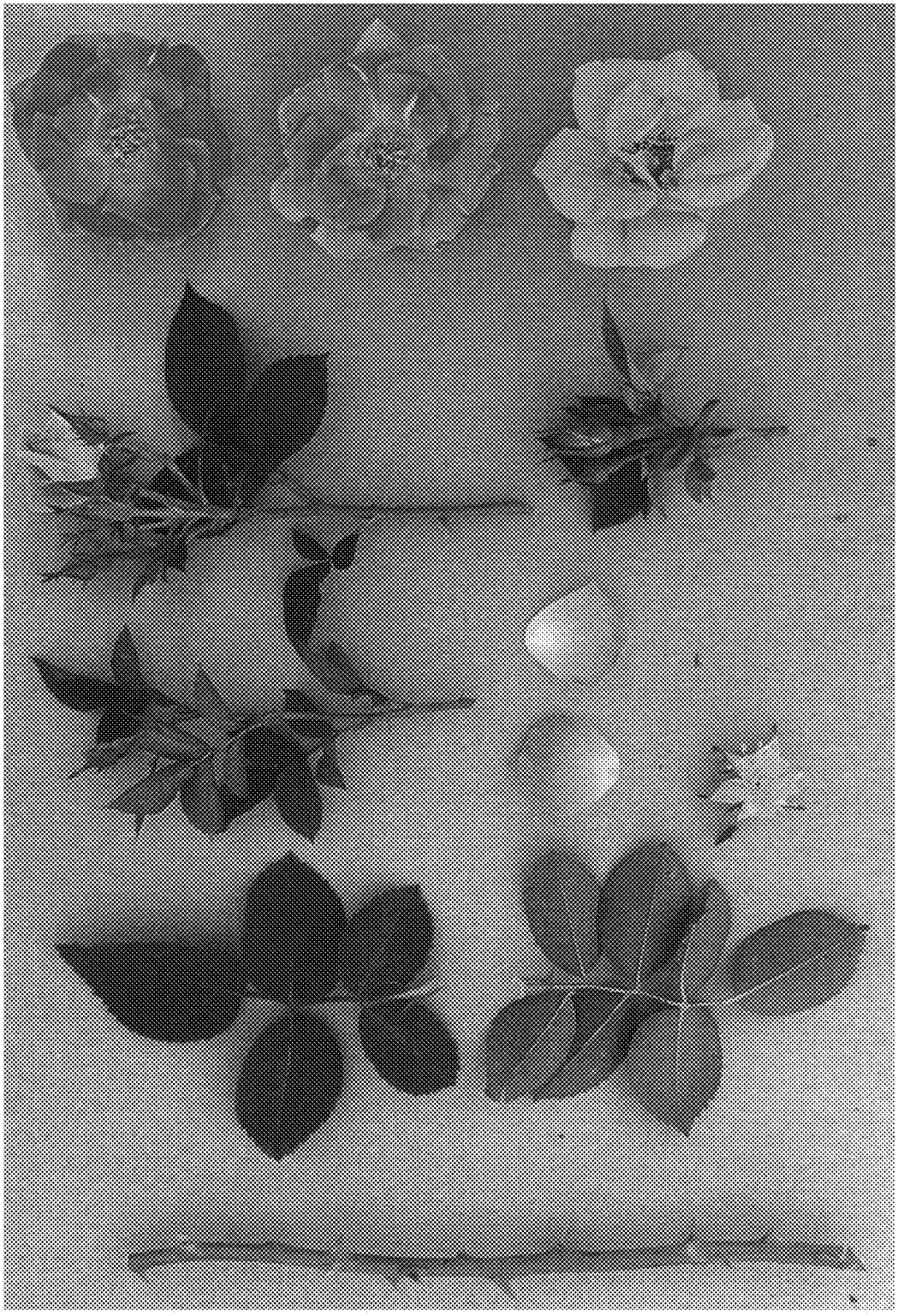

* * * * *